United States Patent [19]

Saito et al.

[11] 4,102,782

[45] Jul. 25, 1978

[54] METHOD OF SAMPLE INTRODUCTION IN THE MICRO LIQUID CHROMATOGRAPHY AND THE APPARATUS THEREFOR

[75] Inventors: Muneo Saito; Hideki Konishi, both of Hachioji, Japan

[73] Assignee: Japan Spectroscopic Co., Ltd., Tokyo, Japan

[21] Appl. No.: 829,296

[22] Filed: Aug. 31, 1977

[30] Foreign Application Priority Data

Sep. 2, 1976 [JP] Japan .................................. 51-105345

[51] Int. Cl.$^2$ ............................................. B01D 15/08
[52] U.S. Cl. .................................. 210/31 C; 210/141; 210/198 C; 73/61.1 C
[58] Field of Search ................. 210/31 C, 141, 198 C; 73/61.1 C

[56] References Cited

U.S. PATENT DOCUMENTS

3,504,799   4/1970   Ogle .................................. 210/198 C
3,575,295   4/1971   Yoshida ........................... 210/198 C

*Primary Examiner*—John Adee
*Attorney, Agent, or Firm*—Browdy & Neimark

[57] ABSTRACT

A method of accurate sample introduction, while holding a good reproductivity, into a chromatographic system by means of employing a pulse-motor as a driving source of a syringe for holding the mobile phase, inversely rotating the same pulse-motor by imparting a certain predetermined number of pulses during the sample collecting or picking-up period in order to cause the syringe to make a sucking action, and making the syringe suck certain predetermined amount of the sample from an open end of a mobile phase supplying line which has been disconnected from the column, and an apparatus for actualizing the method.

8 Claims, 1 Drawing Figure

U.S. Patent
July 25, 1978
4,102,782
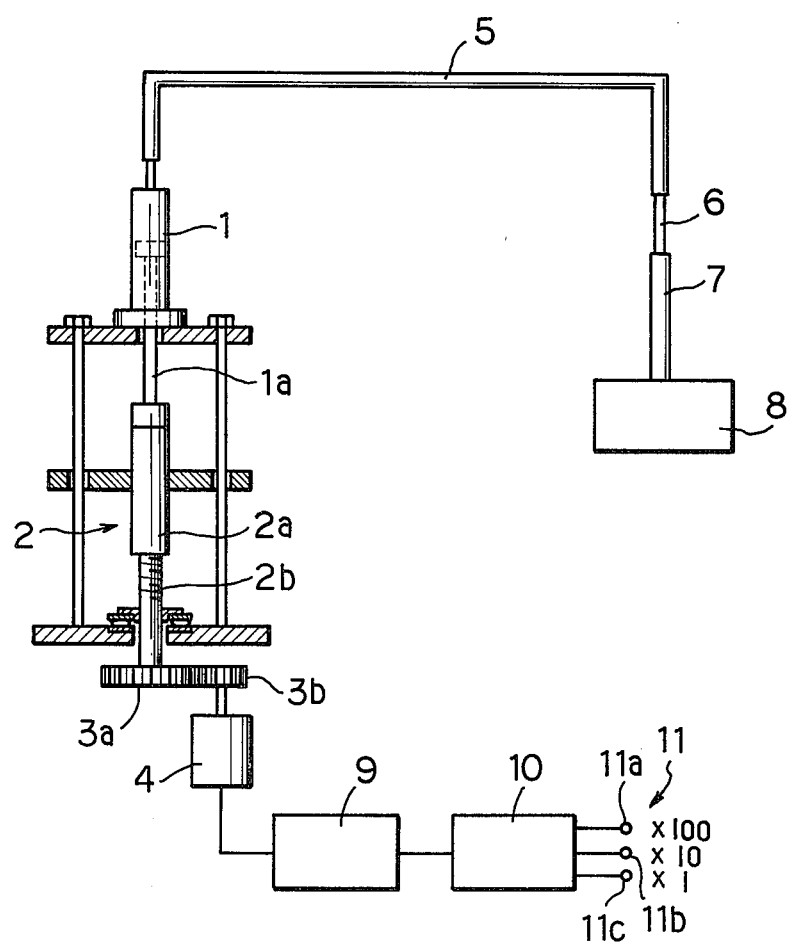

METHOD OF SAMPLE INTRODUCTION IN THE MICRO LIQUID CHROMATOGRAPHY AND THE APPARATUS THEREFOR

BACKGROUND OF THE INVENTION

This invention relates to a method of introducing a sample into the Micro Liquid Chromatography (hereinafter simply called MLC) and an apparatus therefor, more particularly to a method and an apparatus therefor of introducing extremely small amount of the sample accurately and in good reproductivity in a MLC, wherein a micro amount of sample less than 1 µl is introduced for developing the same, by means of employing syringe driven by a pulse-motor, i.e., a stepping motor for the supplying of the mobile phase, causing the syringe by inverse rotation of the pulse-motor which has been given a predetermined number of pulses, and introducing predetermined amount of the sample into the chromatographic system.

In MLC columns less than 1 mm in inside diameter, less than 30 cm in length, for example 10-15 cm, are generally used; and micro analyses of samples less than 1 µl, particularly in the range between 0.01 and 0.3 µl, are usual. Since the flow rate is also so minute as 2-16 µl/min, MLC is generally extremely micro or minute at the present time, and even called the High Speed Micro Liquid Chromatography.

So the conventional ways of sample picking-up and sample introduction in a liquid chromatography, which have been depending upon a micro syringe used for a large-sized liquid chromatography wherein, for example, the inside diameter of the column is in the range of 2-3 mm, the length of the column is in the range of 25-100 cm, and the flow rate is in the range of 0.5-2 ml/min, are not necessarily practicable for the present day liquid chromatography. Those traditional ways of sample introduction, when applied to the abovementioned present day MLC, have many disadvantages as follows:

(1) Since the micro syringe determines the sample amount by the graduation inpressed thereon, it is quite difficult to exactly pick up a micro amount of the sample less than 1 µl and to introduce it into the chromatographic system. Personal variation in the handling amount is also inevitable in this case.

(2) The thickness of a syringe needle in the micro syringe is innegligibly great against the inside diameter of the column less than 1 mm, for example, of 0.5 mm; so the liquid is liable to be so disturbed while the sample is introduced and the needle is removed, as to affect the chromatogram obtained from the development of the sample.

(3) When a micro column of small inside diameter is used for introducing micro amount of the sample, it is required to minimize the dead volume above and below the column to the greatest extent for preventing the diffusion of the sample. In the introduction of the sample by a conventional micro syringe, an injection port is needed to be disposed at the inlet of the column, so it is extremely difficult again to reduce the dead volume here.

SUMMARY OF THE INVENTION

It is therefore a primary object of this invention to provide a highly accurate sample introducing method in MLC and an apparatus therefor including a highly accurate control device, so as to eliminate the abovementioned shortcomings.

It is another object of this invention to provide a method and an apparatus therefor of exactly picking up and introducing a micro amount of the sample into the column in good repreductivity, eliminating the personal variation of the sample amount introduced according to the operator.

Other objects and advantages of this invention will be apparent from the study of the following description in conjunction with the accompanying drawing.

The abovementioned objects of this invention can be attaind by executing the processes summarized under in the order:

(a) a step of removing a mobile phase supplying line (hereinafter simply called supplying line) for transporting the mobile phase retained in the syringe into the column from the column;

(b) a step of immersing an open end of the supplying line into the sample;

(c) a step of inversely rotating the pulse-motor for driving the syringe piston a certain predetermined number of pulses in order to cause the syringe to suck certain predetermined amount of sample into the supplying line;

(d) a step of reconnecting the supplying line to the column; and (e) a step of rotating the pulse-motor in the opposite direction to transport the sucked sample to the column together with the mobile phase.

In accordance with the order of the steps of this invention, the sample is sucked or picked up from the open end of the supplying line due to the sucking action of the syringe, which is used for supplying the mobile phase, by means of utilizing it with the help of a pulse-motor, i.e., a stepping motor being inversely rotated a certain predetermined number of pulses. So the sample amount sucked, that is, the sample amount introduced to the chromatographic system can be mechanically or highly accurately determined by the number of pulsation imparted to the pulse-motor as the number of inverse rotation. It means an exact amount of the sample can be introduced constantly without being varied according to the operator. The amount of the sample picked up and introduced can be controlled simply and in a micro range, by arranging the selecting operation of the number of pulsation to be imparted to the pulse-motor as a single action, for example, by depressing a push-button.

BRIEF DESCRIPTION OF THE DRAWING

The only FIGURE is a schematic diagram of an embodiment of a micro-liquid-chromatographic system.

DETAILED DESCRIPTION OF A PREFERRED EMBODIMENT

In the FIGURE numeral 1 designates a pump syringe retaining a mobile phase medium or solvent. A piston 1a of the pump syringe 1 is drivingly moved in its axial direction by the actuation of a pump driving screw mechanism 2 for transporting the mobile phase in the syringe 1, via a connecting tube 5 and a sample retainer tube 6, into the column 7. The pump driving screw mechanism 2 comprises a cylindrical nut 2a having a tapped portion inside thereof, whose one end being connected to the piston 1a, and a threaded rod 2b, one end of which being threaded into the cylindrical nut 2a for engagement with the tapped portion, the other end of which being connected to a gear 3a. A gear 3b, which is in engagement with the gear 3a, is connected to the pulse-motor 4 for moving the piston 1a in a vertical direction in the FIGURE. The pulse-motor 4 positively rotates, during the normal solvent transporting period, in which it supplies the mobile phase from the syringe 1 to the column 7, at a constant predetermined rate, for moving the piston 1a upwards to cause the mobile phase in the syringe 1 to be discharged; it is inversely rotated a predetermined number of pulses, during the sample picking-up period, due to a signal of the predetermined number of pulses given by a push-button 11, via a pulse calculating means 10 and a pulse-motor driving circuit 9. In this embodiment three grade push-bottons, 11a, 11b, and 11c each being alloted its own preset number of pulses, are provided for selecting the most suitable number of pulsation. Selectively pressing any one of the push-buttons actuates an input to the pulse calculating means 10. The pulse-motor driving circuit 9 will be actuated in response to the number of electric pulses designated by the push-button pressed, whereby the pulse-motor 4 will be inversely rotated for downwardly moving the piston 1a in the FIGURE, via the pump driving screw mechanism 2, which results in causing the syringe 1 to suck the mobile phase. On the other hand, a connecting tube 5 for transporting the mobile phase, connected to the discharging port of the pump syringe 1 on one end thereof, is engaged on the other end thereof with the sample retainer tube 6, the end of which being connected to the column 7. The connection between the retainer tube 6. and the column 7 is tight but detachable so as to be easily connectable or disconnectable, in such a manner as to simply insert the end of the retainer tube 6 into or onto the inlet (open portion) of the column 7. Generally the column used in this invention is an extremely fine tube of the inside diameter less than 1 mm, and made of fluoride polymer, being packed with particles. Such a column is disclosed in an application filed with Ser. No. 725,938 on Sept. 23, 1976 by MOCHIZUKI et al. U.S. Pat. No. 4,059,523, which is being assigned to JAPAN SPECTROSCOPIC CO., LTD just like this application. That column shown as an example in the disclosure can be preferably employed in this invention, too. At the downstream end, the outlet, of this column 7 is disposed a detector 8, which detects each ingredient of the sample devloped in the column 7 for describing the chromatogram.

Picking-up of a sample in such a chromatographic system is carried out in accordance with the following order of steps. Not only the sample retainer tube 6 and the connecting tube 5, but also the pump syringe 1 is filled with sufficient amount of mobile phase for one cycle of analysis, which procedure of filling the mobile phase is (1) to remove first the sample retainer tube 6 from the column 7 for immersing the same in the mobile phase in the tank or container; and (2) to inversely rotate the pulse-motor 4 for a sufficient period of time. If there should be ingress of air during the above process the pulse-motor may be rotated in the positive direction to expel the air out of the system. When sufficient amount of mobile phase is retained within the syringe 1, in a continuous course of analysis, the aforementioned operation is not necessary.

While the supplying line (the connecting tube 5 and the retainer tube 6) is filled with mobile phase the open end of the retainer tube 6 is immersed in the sample solution; the pulse-motor 4 is stationary at this time thereby doing no suction or delivery action. Then, such a number of pulsation as corresponding to the amount of the sample to be picked up (sucked) is selected by pushing any one of the pushbuttons 11 for being input to the pulse calculating means 10. The pulse-motor will be inversely rotated, via the pulse-motor driving circuit 9, just the predetermined number of pulses, which will cause the syringe 1 to make the necessary suction through the pump driving screw mechanism 2. The suction stroke generated in the syringe 1 works, through the connecting tube 5, on the sample suction in the retainer tube 6, resulting in the picking-up of the sample in the predetermined amount. When the sample 6 immersed in the sample solution is raised, and the remnant sample solution remaining around the outer surface of the retainer tube shall be wiped off by a piece of gauze or the like. The open end of the retainer tube 6 shall be again immersed in the mobile phase medium for causing the mobile phase to be sucked very small amount (usually around 0.1 $\mu l$) with the object of sandwiching the sample layer with the mobile phase situated on either side. This sandwiching of the sample with the mobile phase is advantageous in preferably preventing the loss of the sample when the retainer tube 6 and the column 7 is reconnected, which means an introduction of the sample in more exact amount than otherwise into the chromatographic system. The sample retainer tube 6 which is containing the sucked sample shall be reconnected by being inserted into the inlet opening of the column 7. Upon having completed the reconnection of the retainer tube 6 and the column 7, the pulse-motor 4 shall be rotated in the positive direction. The supplying of the mobile phase in the syringe 1 through the connecting tube 5 will necessarily transport the sample into the column 7 for developing the same into each individual ingredient.

Besides, an error of picking-up amount of the sample due to the backlash appearing on screws and gears in the pump screw mechanism or others can of course be held down mechanically to some extent by the prior art, but it is possible to reduce it to a negligible level by means of picking up the mobile phase medium in the same manner as in the sample picking-up case, prior to the sample picking-up. It makes a further enhancement of the reproductivity and a more exact sample picking-up possible.

As described above in greater detail this invention is aimed at, by means of employing a pulse-motor as a driving source of a pump syringe 1, imparting it a certain predetermined number of pulsation for inversely rotating the pulse-motor with the object of controlling the sucking operation of the pump syringe 1. In comparison with the sample introduction operation using a traditional micro-syringe, this invention has succeeded in remarkably reducing the variation of sample introduction according to the analysis operator. In addition, this invention assures an exact picking-up and introduction of micro amount of sample less than 1 $\mu l$, which is greatly effective or worthwhile in the practical field of analysis.

While the invention has been particularly shown and described with reference to preferred embodiment thereof, it will be understood by those skilled in the art that the foregoing and other changes in form and details can be made therein without departing from the spirit and scope of the invention.

What is claimed is:

1. Method of introducing a sample in the micro-liquid-chromatography system, said method comprising:

(a) a step of removing a mobile phase supplying line for transporting the mobile phase retained in a syringe into a chromatographic column from said column;

(b) a step of immersing the open end of said removed mobile phase supplying line;

(c) a step of rotating a pulse-motor in a direction for driving a piston of said syringe a certain predetermined number of pulses in order to cause the syringe to suck predetermined amount of sample into said mobile phase supplying line;

(d) a step of re-connecting said mobile phase supplying line to said column; and (e) a step of rotating said pulse-motor in the opposite direction to transport the sucked sample to said column together with the mobile phase.

2. Method in accordance with claim 1, wherein said predetermined number of pulses can be imparted to said pulse-motor by means of a single or one touch action of an analysis operator.

3. Method in accordance with claim 1, wherein the removal of said mobile phase supplying line from said column is carried out between a sample retainer tube disposed at an extreme end of said mobile phase supplying line and said column, and certain predetermined amount of sample can be retained in said sample retainer tube due to sucking action by said syringe.

4. Method in accordance with claim 1, wherein the mobile phase is filled in said syringe and said mobile phase supplying line prior to the sucking of the sample into said mobile phase supplying line.

5. Method in accordance with claim 1, wherein the mobile phase is sucked into said mobile phase supplying line after certain predetermined amount of the sample has been sucked in order to keep the sample sandwiched by said mobile phase and said mobile phase supplying line is re-connected to said column.

6. Method in accordance with claim 1, wherein the mobile phase is, prior to the suction of the sample into said mobile phase supplying line, sucked into said mobile phase supplying line just in the same way as that of sample sucking defined in claim 1.

7. In a chromatographic system including a syringe for retaining a mobile phase, a connecting tube which is connected to said syringe for transporting the mobile phase discharged from said syringe into a chromatographic column, and a sample retainer tube disposed between said connecting tube and said column, a sample introducing apparatus for a micro-liquid-chromatography comprising (a) a detachable connection mechanism employed between said column and said sample retainer tube;

(b) a driving mechanism with a pulse-motor, being capable of positive and inverse rotation, for reciprocating a piston in said syringe in the axial direction thereof; and (c) a mechanism for imparting predetermined number of pulses to said pulse-motor in order to inversely rotate said pulse-motor for causing predetermined amount of sample to be sucked into said sample retainer tube.

8. The sample introducing apparatus in accordance with claim 7, wherein said mechanism for imparting a predetermined number of pulses to said pulse-motor further comprising (a) means permitting an operator to select a predetermined number of pulsation; (b) a pulse calculating means for giving electric pulse of the selected number of pulsation; and (c) a driving circuit for inversely rotating said pulse-motor by means of electric pulse which is input from said pulse calculating means.

* * * * *